United States Patent [19]
Hansen et al.

[11] Patent Number: 5,198,339
[45] Date of Patent: Mar. 30, 1993

[54] METHOD FOR DETECTION OF GRAM-NEGATIVE BACTERIAL LIPOPOLYSACCHARIDES IN BIOLOGICAL FLUIDS

[75] Inventors: Eric J. Hansen, Plano; Robert S. Munford, Dallas, both of Tex.; Jussi Mertsola, Kaarina, Finland

[73] Assignee: Board of Regents, The University of Texas System, Austin, Tex.

[21] Appl. No.: 553,072

[22] Filed: Jul. 13, 1990

[51] Int. Cl.⁵ .................... G01N 33/53; G01N 33/579
[52] U.S. Cl. ..................... 435/7.2; 435/7.91; 435/7.32; 435/7.35; 435/810; 435/879; 435/7.37; 435/7.92; 435/7.94; 435/23; 435/24; 436/501; 436/518; 436/71; 436/815; 436/821
[58] Field of Search .................. 435/7.91, 7.2, 7.32, 435/7.35, 810, 879, 23, 24; 436/501, 502, 518, 71, 815, 821

[56] References Cited

FOREIGN PATENT DOCUMENTS 0217527 4/1987 European Pat. Off. .
279517 8/1988 European Pat. Off. .
0291856 11/1988 European Pat. Off. .

Primary Examiner—Esther L. Kepplinger
Assistant Examiner—Toni R. Scheiner
Attorney, Agent, or Firm—Arnold, White & Durkee

[57] ABSTRACT

The invention relates to a method of detecting gram-negative bacterial endotoxin using antibody capture combined with amoebocyte lysate chromogenic detection. The method is highly sensitive and rapid and may be used for detection of specific endotoxin. In a particular application, picogram levels of *Haemophilus influenzae* are detected in plasma taken from previously infected mammals.

23 Claims, 2 Drawing Sheets

METHOD FOR DETECTION OF GRAM-NEGATIVE BACTERIAL LIPOPOLYSACCHARIDES IN BIOLOGICAL FLUIDS

The United States Government may have certain rights in the present invention pursuant to the terms of Grant No. HD22766 awarded by the National Institutes of Health.

BACKGROUND OF THE INVENTION

1. Field of the Invention

The present invention relates to a method for the detection of bacterial endotoxin in a biological fluid or in a fluid intended for clinical or pharmaceutical use, using antibodies cross-reactive with a broad range of gram-negative bacteria to act as lipopolysaccharide capture agents. In particular, the method provides a sensitive assay that can be tailored to detect the endotoxin of selected gram-negative bacteria.

LIST OF ABBREVIATIONS

| LIST OF ABBREVIATIONS | |
| --- | --- |
| Haemopilus influenzae type b | Hib |
| lipooligosaccharide | LOS |
| polymyxin B | PMB |
| immunolimulus | IML |
| chromogenic Limulus amoebocyte assay | CLAL |
| Limulus amoebocyte lysate | LAL |
| lipopolysaccharide | LPS |
| monoclonal antibodies | MAbs |
| enzyme-linked immunosorbent assay | ELISA |
| outer membrane vesicles | OMV |
| sodium dodecyl sulfate | SDS |
| polyacrylamide gel electrophoresis | PAGE |
| pyrogen-free | pf |
| immunoglobulin G | IgG |
| phosphate buffered saline | PBS |
| Tween 20 | Tw |
| bovine serum albumin | BSA |
| cerebrospinal fluid | CSF |
| colony forming units | CFU |
| brain heart infusion broth supplemented with Levinthal base | BHIs |

2. Prior Art in the Field

Septicemia is a potentially fatal clinical condition which is currently increasing in importance, possibly because of the longer survival of immunocompromised patients and greater use of invasive techniques in medicine (1,2). It has been estimated that the incidence of this disease has increased ten-fold during the last 20 years and that the number of cases annually is from 100,000 to 300,000 in the United States alone (3). From 20% to 40% of the patients with gram-negative bacterial septicemia have shock and, of these, approximately 75% will die (1). In children, *Haemophilus infuenzae* type b (Hib) is responsible for about 40% of cases of septic shock (4). *Pseudomonas aeruginosa* bacteremia in neutropenic patients is a particularly virulent form of septicemia.

Specific laboratory diagnosis of gram-negative septicemia is usually performed by culturing blood samples. These methods, however, are relatively slow, requiring several hours to days to detect bacterial growth.

Endotoxin is considered to be a key element in the initiation of the inflammatory cascade during gram-negative bacterial infections (5). Therefore, quantitation of these molecules in blood samples of septic patients has been considered to be important. An easy and highly sensitive way to detect endotoxin involves the Limulus amoebocyte lysate (LAL) assay (6). The LAL assay, however, has several problems which have limited its usefulness in the diagnosis of septicemia. This assay is sensitive to trace amounts of LPS contamination in laboratory fluids and reagents, which then cause false-positive reactions. Furthermore, plasma of patients has several nonspecific activators and inhibitors of the enzymes involved in the LAL reaction Finally, the color and turbidity of normal plasma impedes the high sensitivity of a recent refinement of the LAL method known as the CLAL assay. The latter method measures color generated by the action of activated lysate enzymes on a synthetic chromogenic substrate. Because of these problems, the sensitivity and specificity of the LAL and CLAL assays are thought to be suboptimal for reliable clinical diagnosis.

The basic structure of lipopolysaccharide (LPS) involves three relatively well defined regions and is similar in all gram-negative bacteria. These regions are an O-specific side chain, the core oligosaccharide, and lipid A. The O-specific region is composed of repeating oligosaccharide units each having 2-6 saccharides. The core lies between the O-specific side chains and lipid A and is a branching oligosaccharide having representative sugars such as glucose, N-acetylglucosamine and galactose. In the core region proximal to Lipid A, heptose and keto-deoxyoctonate are commonly found. There is considerable structural variation among the gram-negative bacteria in the O-chain region, but only minor variation throughout the core region with structure being highly conserved in the inner core region proximal to Lipid A. The most highly conserved portion of the LPS molecule is lipid A, a phosphorylated glucosamine disaccharide, to which long chain fatty acids are attached.

Some gram-negative bacteria, including *Haemophilus infuenzae, Neisseria meningitidis, N. gonorrhoeae* and *Bordetella pertussis*, synthesize a different type of LPS molecule that has been designated as lipooligosaccharide (LOS). This LOS molecule is very similar to the LPS molecule except that LOS does not have an O-antigen but consists of lipid A and core oligosaccharide. This LOS molecule is, like LPS, an endotoxin.

The general structure of a typical gram-negative lipopolysaccharide, *S. typhinurium*, is shown in FIG. 1.

Realization that the core region of bacterial lipopolysaccharide is highly conserved has resulted in a search for antibodies that will cross react with the endotoxin of all gram-negative species. Some claimed highly cross reactive monoclonal antibodies have been obtained, for example, several of which are directed toward Lipid A (7-9). Monoclonal antibodies binding specifically with *Escherichia coli* strains have been produced by immunization of mice with bacterial mutants lacking the O-side chain and part of the core polysaccharide (10). At least some of the reported monoclonal antibodies have cross reactivity in detecting bacterial endotoxin despite the fact that in many instances cross reactivity has not been convincingly demonstrated (1). Theoretically, antibodies to the LPS core of any one or at most a few gram-negative bacteria should interact with all gram-negative bacteria having the general core structure of LPS shown in FIG. 1.

XMMEN-OE5 produces a monoclonal antibody that binds epitopes on LPS associated with the endotoxin core glycolipid of gram-negative bacteria (11). The disclosed antibody has broad cross reactivity with gram-negative bacteria of different genera and effectively neutralizes endotoxin. Potential assays using this monoclonal antibody has been suggested, including quantification using standard ELISA techniques well known to those skilled in the art. However, standard methods in immunodiagnosis lack the high sensitivity of the Limulus assay.

The ability of the amoebocyte lysate used in the CLAL assay to react with gram-negative endotoxin has been used to develop an assay for detecting lipopolysaccharides. Endotoxin is bound to a capture agent prepared from an amoebocyte lysate (12). The bound endotoxin is then detected, for example, by antigenic analysis. The limit of detection for *Escherichia coli* K235 LPS by this method was 10 ng. The claimed method appears to be selective for gram-negative endotoxin, but it is far less sensitive than the CLAL assay which can detect picogram quantities. The general utility of the claimed method is therefore limited due to its lack of sensitivity, especially in clinical applications where it is important to detect even very small amounts of LPS or very small numbers of bacteria. Furthermore, very low limits of detection are critical in analysis of sterile solutions for in vivo use.

Thus, there is a need for a general method of detection of bacterial endotoxin which is rapid, specific and sensitive at least to picogram quantities. A versatile assay in principle capable of detecting several different gram-negative pathogens would be particularly useful in clinical situations where the identity of the microorganism as a gram-negative bacterium would determine the specific course of treatment.

SUMMARY OF THE INVENTION

The present invention is a sensitive and selective method for the detection of bacterial endotoxins. The method combines the use of monoclonal or polyclonal antibodies as capture agents and the known sensitivity of the chromogenic Limulus amoebocyte lysate detection system.

Generally, detection of bacterial endotoxin includes the steps of attaching antibodies of the desired specificity to a solid surface, incubating the surface with a sample suspected of containing endotoxin, washing the matrix-bound endotoxin, adding and incubating the bound endotoxin with Limulus amoebocyte lysate and finally adding a substrate of the lysate to form a product that can be measured and is proportional to the amount of any endotoxin present in the sample.

Attachment of antibodies to a solid surface is commonly used for immobilization and is most often achieved by simply coating a hard surface with the antibodies. The antibodies can be attached to any solid surface to which they will adhere. In usual practice, antibodies are adsorbed to the plastic surface of microtiter plate wells, but adsorption could be to any suitable surface. It is important to block uncoated sites to prevent nonspecific binding of interfering substances from the sample. This is normally done with proteins, for example, albumin, but other surface blocking agents that do not interfere with the assay could be used. Excess blocking agents are washed from the surface after reacting with nonspecific binding sites. The wash solution is usually pyrogen-free phosphate buffered saline (pf-PBS) containing Tween 20. It is likely that the presence of detergent increases washing effectiveness. It should be noted that where amoebocyte lysate was used as the capture agent, washing the surface with surfactants such as polyoxyethylene sorbitan monolaurate or deoxycholate caused high levels of nonspecific binding to the immobilized lysate (12); however, that system differs from that of the present invention in that the immobilized lysate is used for capture, not detection. It is possible that detergents may affect antibody capture binding, but in view of the high sensitivity of the method, detrimental effects appear unlikely.

The inventors have found that selection of appropriate antibodies determines the broadness or narrowness of detection of specific endotoxins. Although any cross-reactive antibodies can be used as capture agents for bacterial endotoxin, it is preferable to use a limited number of monoclonal antibodies directed toward the highly conserved region of endotoxin core glycolipid in detecting lipopolysaccharide (LPS) and lipooligosaccharide (LOS) from a wide range of gram-negative bacteria. This includes intact bacteria as well as vesicles or blebs shed or exposed on bacteria and to which the capture antibodies can bind. Examples, not intended to be limiting, of bacteria which could be detected include Escherichia, Bordetella, Branhamella, Salmonella, Haemophilus, Klebsiella, Proteus, Enterobacter, Pseudomonas, Pasteurella, Acinetobacter, Chlamydia and Neisseria and in general any bacteria whose LPS is capable of binding to the selected antibodies.

The practitioner will appreciate that the purpose of the antibodies is to act as capture agents in selectively binding endotoxin, a toxic component of the gram-negative bacterial membrane. There are thus several choices of antibodies. For example, a surface could be coated with antibodies directed specifically to the core oligosaccharide distal to lipid A in any species of gram-negative bacteria. Capture specificity would be then directed toward one or a limited group of bacteria, depending on cross reactivity. On the other hand, antibodies directed toward epitopes proximal to lipid A or to lipid A itself would be expected to display broad cross reactivity toward virtually all classes of gram-negative bacteria.

Selection of the monoclonal antibodies to be used as capture agents is an aspect of this invention that shows its versatility. For example, to detect a range of bacterial endotoxin from several species, one could select antibodies to lipid A or the lipid A/KDO region of LPS since this core region is highly conserved among gram-negative bacteria. Some experimentation may be necessary to obtain an optimal panel of MAb, but there are several references with detailed procedures for producing antibodies of good cross reactivity (7,13-14,16). At least two clones found to secrete monoclonal antibody stably are available as hybridomas XMMEN-OE5 and XMMEN-LY1 and are on deposit with the American Type Culture Collection with respective ATCC Accession Nos. HB9081 and HB9082 (11). The monoclonal antibodies produced by these cell lines show broad cross reactivity against gram-negative bacteria and could be used as capture agents for detecting bacterial endotoxin.

Antibodies could also be developed using experimental techniques known to those skilled in the art. In particular, the antibodies could be selected from hybridomas obtained from immunizations and hybridoma fusions involving several species of rough mutants of gram-negative bacteria. Rough mutants can be selected from wild-type colonies on the basis of their appearance which contrasts with the smooth appearance of wild-type colonies. The rough appearance is the result of deletion of O-antigen. As a result of the deletions, portions of the core become more exposed, enabling formation of a wider selection of antibodies directed to epitopes in the exposed regions. Most preferred monoclonal antibodies would be specific for lipid A or perhaps alternatively a smaller fragment of lipid A.

To assure detection of a wide range of bacterial endotoxin, a panel of 3-4 monoclonal antibodies would be selected, preferably those directed toward heptose/KDO regions of the core. This region is adjacent to lipid A and comprises several unusual 2-keto sugars, particularly 3-deoxy-D-manno-octulosonic acid (KDO). Selected antibodies could include MAbs 4-7B5 (7), 8A1 (9), 7G (16), A6(H4C5) (15) and 8-2C1 (7). The broadly cross-reactive monoclonal antibody produced by hybridoma cell line XMMEN-OE5 (ATCC Accession No. HB9081) would also serve as a capture agent, either in combination with the other antibodies or, depending on the degree of cross reactivity required, by itself (11).

The sample in which bacterial LOS or LPS is to be detected is usually a body fluid such as plasma, serum, cerebrospinal fluid, urine, saliva, urethral secretions, sputum or the like, all being fluids that normally either are sterile or do not contain the organism of interest. The method is, however, of general application and could be used to detect endotoxin contamination in sterile preparations, and in fluids intended for clinical or pharmaceutical use or in food products.

Samples to be tested for endotoxin may need to be diluted, usually with pyrogen-free diluent, preferably phosphate-buffered saline. Dilution would depend on the type of sample and on the amount of endotoxin present. In any event, prior to incubation with the immobilized capture antibody, the sample for testing is subjected to heat treatment, preferably at 75° C. for about 12 min, in order to inactivate materials that would later interfere with the Limulus chromogenic assay. Heating may also facilitate exposure of binding sites to the capture agent.

Once the sample is prepared for analysis, it is then incubated with the capture antibody or antibodies. When microtiter plate wells are used, this is simply a matter of adding a measured amount of sample to the wells and incubating for a time sufficient for binding to occur, usually about an hour incubation at 37° C. Other incubation times might work, and shorter times could possibly be used depending on the species of endotoxin detected. Incubation could also be performed at room temperature, although longer times to effect binding might be necessary.

Measurement of endotoxin is accomplished by adding an agent capable of detecting the protease release stimulated by the presence of endotoxin. Amoebocyte lysate contains factors which in the presence of endotoxin initiate a cascade that releases, among others, serine proteases. A most preferred source of lysate is the blood of *Limulus polyphemus,* but other organisms may be used, for example *Tachypleus tridentatus.* Adding a protease substrate, usually a chromogenic compound, to the lysate sample containing endotoxin allows cleavage of the substrate and release of a chromophore which can be detected spectrophotometrically. The amount of protease activated is proportional to the amount of endotoxin bound by the capture monoclonal antibody and thus the resultant color (optical density) will be proportional to the amount of endotoxin present in the sample. In a preferred embodiment, the chromogenic substrate is N-benzoyl-val-arg-p-nitroanilide in which the released C-terminal chromogenic moiety is measured at 410 nm. Other chromogens could be used, for example tetramethylbenzidine, or different p-nitroanilide substrates. Quantitation could also be effected using other labels and other detection means, including fluorescent and isotopic labels or initiation of secondary reactions so long as the reaction is proportional to the protease activated by the endotoxin. A standard curve can be generated using a purified endotoxin or, preferably, the U.S. standard endotoxin as the standard.

In a particular example of the invention, the specific detection of *Haemophilus influenzae* endotoxin in biological fluids is demonstrated. The capture monoclonal antibody is bound to a matrix, typically plastic microtiter wells, which is then blocked with a protein, usually bovine serum albumin, but in a preferred embodiment with fetal calf serum. Any Hib LOS endotoxin present in the sample will be bound to the capture antibody and not to unexposed surface. In a preferred embodiment, the capture agent comprises two monoclonal antibodies, one (12D9; ATCC Accession No. HB10462) directed against an epitope in the oligosaccharide region of Hib LOS DL26 and the other (4C4; ATCC Accession No. HB10461) directed against an epitope in the oligosaccharide region of Hib LOS DL42 (20). Both are IgG3 type immunoglobulins. A single capture agent, 4C4, could be used but not all strains of Hib would be detected.

After contacting the test sample with the matrix-bound monoclonal antibody, bound Hib LOS is washed to remove nonbinding substances present, preferably with pf-PBS containing a detergent such as Tween 20. In a subsequent step, the surface-bound Hib LOS is incubated with an amoebocyte lysate, preferably Limulus amoebocyte lysate. The incubation is usually performed at 37°, allowing activation of a protease system from the lysate by bound endotoxin. In a final step, a chromogenic substrate is added and the optical density of the sample is read after standing at room temperature, preferably for 30 minutes. Optical density may be read on a spectrophotometer, such as the ELISA reader. LOS standards are included on the test plate and from them concentrations of endotoxin in the samples determined.

The method is simple and rapid. Tests can be completed within two hours after sample preparation. Typically, the sample is incubated with the capture antibody for an hour at 37° C., washed, incubated about 20 min at room temperature with amoebocyte lysate and further incubated at room temperature after addition of chromogenic substrate. Thus measurements may be made within three hours of incubating the sample in microtiter wells coated with capture antibody.

The inventors have demonstrated the specificity of the invention with Hib LOS detection; however, it will be appreciated that other pathogens of clinical importance could be detected using appropriate antibodies. For example, the method is readily adapted to specific detection of *Pseudomonas aeruginosa* and *Pseudomonas maltophilia* by employing the monoclonal antibody XMMPS-605 produced by the hybridoma cell line having ATCC Accession No. HB8909 (11). The development of other specific diagnoses is limited only by the availability of the capture antibody or antibodies required and not by the general applicability of the method.

It is contemplated that one or more kits will be useful for the practice of the method of the present invention. Such kits would contain separate containers comprising monoclonal antibodies suitable for the detection of all or a limited selection of bacterial endotoxins. In addition, containers comprising an amoebocyte lysate and a chromogenic substrate to detect release of lysate protease would be provided, all preferably in lyophilized form. In one particular kit for detection of bacterial endotoxin, the monoclonal antibody from hybridoma cell line XMMEN-OE5 alone or in combination with one or more of the monoclonal antibodies 4-7B5, 8A1, A6 and 8-2C1 would be provided. For the determination of *Haemophilus influenzae* MAb 4C4 and MAb 12D9 would be provided.

DETAILED DESCRIPTION OF THE PREFERRED EMBODIMENTS

Figure 1:
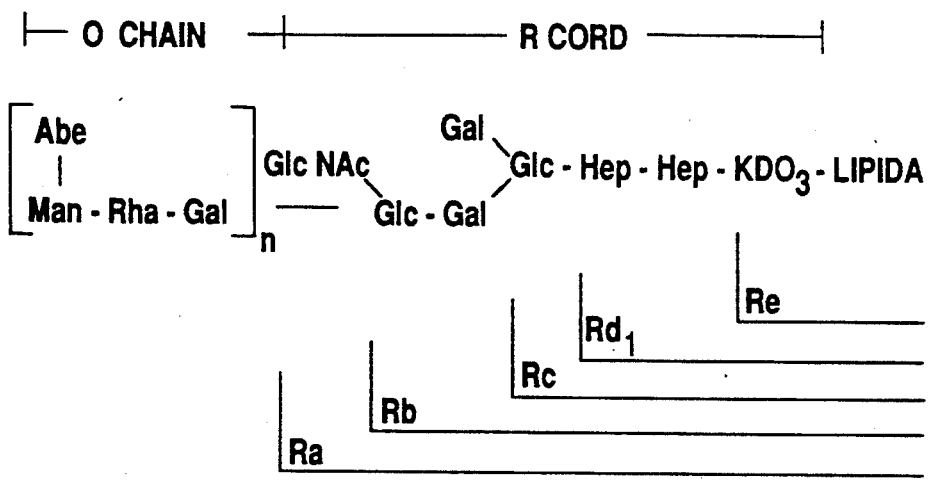
FIG. 1 shows the structure of *S. typhimurium* lipopolysaccharide which is similar to the lipopolysaccharide of other gram-negative bacteria $R_a$, $R_b$, $R_c$, $R_{d1}$ and $R_e$ designate the structures of LPS molecules synthesized by different mutants of Samonella.

As discussed above, the invention is a sensitive and rapid assay that can be designed to detect gram-negative bacterial endotoxin, or, modified to detect specific species of bacterial endotoxin. In particular, the method is useful for detection of very low levels of endotoxin.

The inventors have used antibodies as the basis of selectivity of their method and combined the previously known reaction with amoebocyte lysate to provide an assay that is highly sensitive. The antibodies are preferably monoclonal antibodies directed to designated regions of the endotoxin core of LPS/LOS. As an example of how the method is practiced, the following details refer particularly to the detection of *Haemophilus influenzae* type b endotoxin (Hib LOS); however, analogous considerations apply to detection of other species with different antibodies, one or more, being used. An inclusive method to detect gram-negative bacterial endotoxins, for example, would require up to several monoclonal antibodies directed to regions at or very close to the endotoxin lipid A core. A method to detect *Pseudomonas aeruginosa* could employ monoclonal antibody XMMPS-605 (ATCC Accession No. HB8909 (11)).

MATERIALS AND METHODS

Bacterial Strains and Culture Conditions. Hib strain DL42 has been characterized extensively (17). Another Hib strain (DL301) used in this study was a recent isolate from a child with Hib meningitis in Dallas. Both of these strains belong to Hib LOS antigenic group 2, as determined by their reactivity with MAb 4C4 in the colony blot-radioimmunoassay stem (17). Encapsulated *Escherichia coli* K1 (77-436) and Hib strain DL26, from Hib LOS antigenic group 1 (17) were used for control experiments. These strains do not react with MAb 4C4.

Hib strains were grown in brain-heart infusion medium (Difco Laboratories, Detroit, Mich.) supplemented with Levinthal's base (BHIs) as previously described (18). *Escherichia coli* K1 was grown in brain-heart infusion medium without the supplement.

Endotoxins. LOS from Hib strain DL42 was purified by means of the modified hot phenol-water method (19). Purified LOS was diluted in pyrogen-free saline (Abbott Laboratories, North Chicago, Ill.) and stored in 1 μg/ml concentrations at −70° C. until used as a standard in the assays. LPS purified from *Escherichia coli* O11:B4 (Sigma NO. L-33012) was purchased from Sigma Chemical Company, St. Louis, Mo., as were LPS from *Escherichia coli* 0127:B8 (Sigma No. L-3137), *Klebsiella pneumoniae* (Sigma No. L-1770) and *Pseudomonas aeruginosa* (Sigma No. L-8643).

Monoclonal Antibodies (MAbs). MAb 4C4 (ATCC Accession No. HB10461), directed against an epitope in the oligosaccharide portion of the LOS molecules of Hib strains belonging to Hib LOS antigenic group 2, has been described previously. This MAb reacts with the LOS from Hib strains DL42 and DL301 and, additionally, was able to recognize 86% of the Hib clinical isolates recently tested (17).

Other Materials. Sterile polystyrene ELISA plates were purchased from Corning Laboratory Sciences, Houston, Tex. All plates were determined to be pyrogen-free prior to use. Each vial of LAL (Pyrotell, Associates of Cape Code, Woods Hole, Mass. specified to be suitable for use in the CLAL) was reconstituted with 10 ml of pf-water, and stored in multiple portions at −20° C. for less than 3 months. For the IML assay, the LAL was diluted with 20 ml of pf-water. N-benzoyl-val-gly-arg-p-nitroanilide hydrochloride (Sigma No. B-4758) was diluted to a concentration of 0.7 mg/ml in pf-water and stored at 4° C. until used in the assays.

Statistical Analysis. Pearson's correlation coefficient was used to assess the strength of the relationship between the results from the CLAL and IML assays and the magnitude of bacteremia in the animals.

The following examples are intended by way of illustration of specific embodiments of the present invention and are not intended to be limiting to the extent of describing all possible embodiments. Those skilled in the field will recognize that modifications could made to the disclosed methods and applications that would remain within the scope of the present invention.

EXAMPLE 1

Immunolimulus Assay for Hib LOS Using Purified Hib LOS and Bacteria

Microtiter plates were coated overnight at room temperature with MAb 4C4 diluted 1:500 in 0.1 M sodium carbonate buffer, pH 9.6 (20). The microtiter wells were washed three times with pf-PBS containing 0.05% (v/v) Tween 20 (pf PBS-Tw) and then blocked with 1% (vol/vol) fetal calf serum (20) in carbonate buffer for one hour at 37° C. The plates were again washed three times with pf-PBS-Tw. Plasma for dilution of purified LOS samples was obtained by collecting blood by cardiac puncture from 50 normal infant rats, centrifuging and pooling the plasma. Plasma aliquots were stored at −70° C. and prior to use as diluent were diluted 1:3 in pyrogen-free phosphate buffered saline (pf-PBS, pH 7.4). Purified Hib DL42 LOS was diluted in pf-PBS and in plasma:PBS (diluted 1:3) and Hib bacteria were diluted in plasma:PBS (diluted 1.3). Purified Hib LOS standards were prepared in 0-1,000 pg/ml concentrations in the appropriate dilution fluid. After heat-inactivation at 75° C. for 12 min, 50 μl of the test samples and the standards were incubated in the microtiter wells, for one hour at 37° C. The wells were washed six times with pf-PBS-Tw and then filled with 50 μl LAL extract in pf-water. After 20 minutes incubation at room temperature, 50 μl of the chromogenic substrate was added and the plates were incubated 30 minutes at room temperature. The optical density was then measured using the ELISA reader and the concentrations of LOS in the test samples were obtained from the standards included on each plate.

Figure 2:
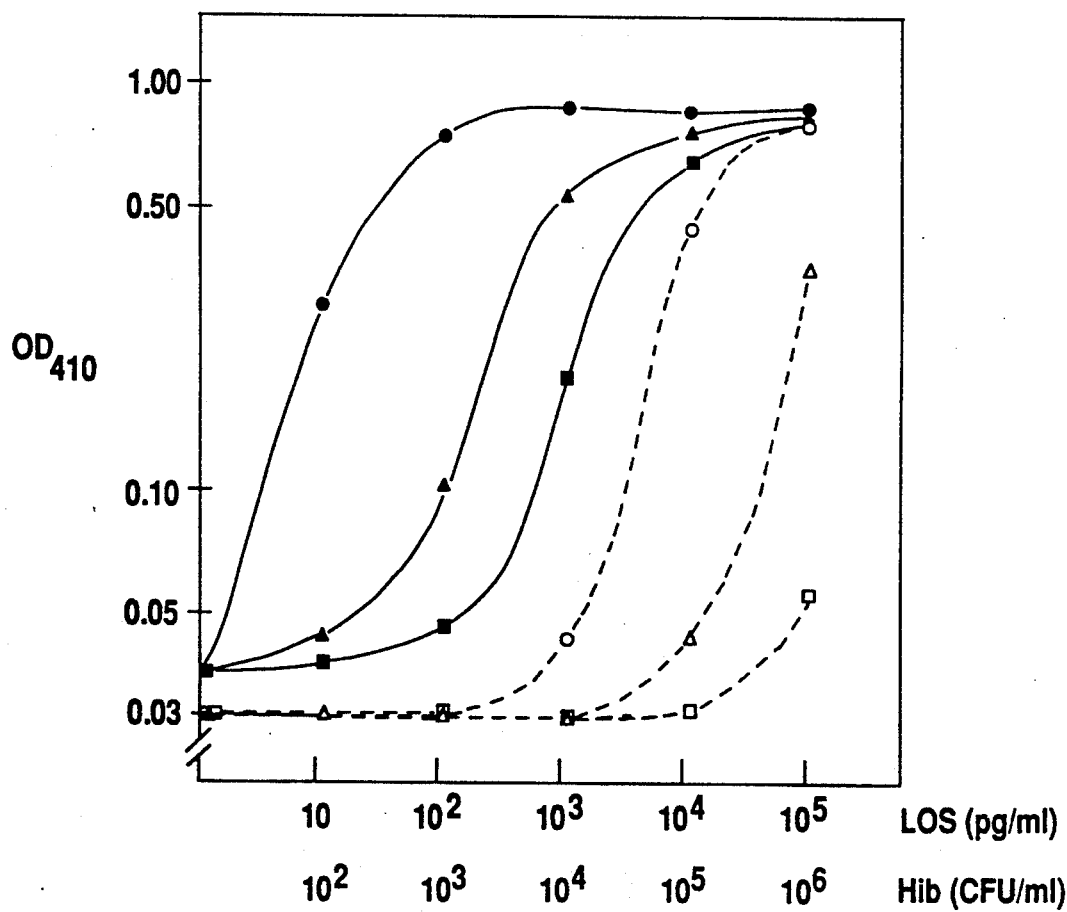
FIG. 2 indicates the detection of Hib DL42 LOS in PBS (●) and in plasma-PBS (diluted 1:3) (▲) and Hib DL42 bacteria in plasma-PBS (diluted 1:3) (■) by immunolimulus assay. Open symbols indicate nonspecific background. Results are means from duplicate wells.

The limit of sensitivity (the concentration of LOS yielding an optical density reading exceeding the mean +2SD of the background) was 2 pg/ml in pf-PBS and 10 pg/ml in diluted plasma (FIG. 2). The sensitivity of the IML method in detecting LOS in diluted plasma containing various numbers of Hib organisms corresponded to a concentration of 300 CFU/ml, respectively.

The specificity of the IML assay is based on its ability to detect only those LOS molecules bound to the solid phase by the MAbs. As shown in FIG. 2, the nonspecific background (obtained with wells without MAb) remained consistently low during testing of plasma samples when the concentration of LOS was less than 1,000 pg/ml or when the concentration of bacteria was less than $10^5$ CFU/ml. With higher concentrations of either LOS or Hib the background increased and the IML assay lost its antibody-dependent specificity although it showed the presence of endotoxin with the CLAL-type reaction. The specific antibody binding could be demonstrated in these cases with the further dilution of the test samples.

EXAMPLE 2

Immunolimulus Assay for Purified Hib LOS in Plasma

Purified Hib DL42 LOS and purified LPS samples from four different gram-negative enteric bacteria were added in varying concentrations to normal infant rat plasma, diluted 1:3 in PBS, then heated at 75° C. for 12 min. The samples were tested with the immunolimulus assay as detailed in Example 1. Results are shown in Table 1 and indicate a high degree of specificity for the IML assay system. At LPS concentrations of less than or equal to 10 ng/ml, the optical density results were at background level; at higher concentrations, the results showed only non-specific reactions.

TABLE 1

Detection of Hib LOS by immunolimulus assay in normal infant rat plasma samples containing different concentrations of LOS/LPS.

| Strain | | Concentration of LOS/LPS in Plasma | | |
|---|---|---|---|---|
| | | 100 ng/ml | 10 ng/ml | 1 ng/ml |
| Hib DL42 | A[a] | 0.873[d] | 0.078 | 0.515 |
| | B[b] | 0.412 | 0.073 | 0.030 |
| | C[c] | 0.461 | 0.635 | 0.485 |
| E. coli O:111 | A | 0.278 | 0.027 | 0.027 |
| | B | 0.322 | 0.031 | 0.028 |
| | C | 0 | 0 | 0 |
| E. coli O:127 | A | 0.333 | 0.029 | 0.027 |
| | B | 0.409 | 0.030 | 0.026 |
| | C | 0 | 0 | 0.001 |
| K. pneumoniae | A | 0.044 | 0.027 | 0.027 |
| | B | 0.043 | 0.028 | 0.026 |
| | C | 0.001 | 0 | 0.001 |
| P. aeruginosa | A | 0.160 | 0.029 | 0.029 |
| | B | 0.147 | 0.030 | 0.028 |
| | C | 0 | 0 | 0.001 |

[a]Optical density obtained from wells coated with MAb 4C4
[b]Optical density obtained from wells lacking MAb 4C4 (control for nonspecific binding)
[c]Difference between wells A and B
[d]Results are means from duplicate wells

EXAMPLE 3

Immunolimulus Assay for Hib LOS in Plasma from Rats Infected with Hib

Five-day old infant rats were infected intranasally with $1-3 \times 10^8$ colony forming units (CFU) of Hib as described (19). For control experiments with Escherichia coli K1, the rats were infected by intraperitoneal inoculation with 100 or 1,000 CFU in 0.1 ml PBS. Blood cultures were obtained by taking 10 μl of blood from the tail vein at various time points (15–48 hours) after bacterial challenge. The magnitude of bacteremia was determined by spreading blood samples on BHIs-agar plates. Immediately after the blood sampling from the tail vein, cardiac puncture was performed on the same animals anesthetized with ether and blood was collected in syringes containing 3.8% (wt/vol) sodium citrate (0.05 ml of sodium citrate/0.5 ml of blood). Blood was centrifuged at 5,000 rpm in an Eppendorf centrifuge for 10 minutes at room temperature and plasma was transferred to polypropylene screw-cap tubes and stored at −70° C.

Figure 3:
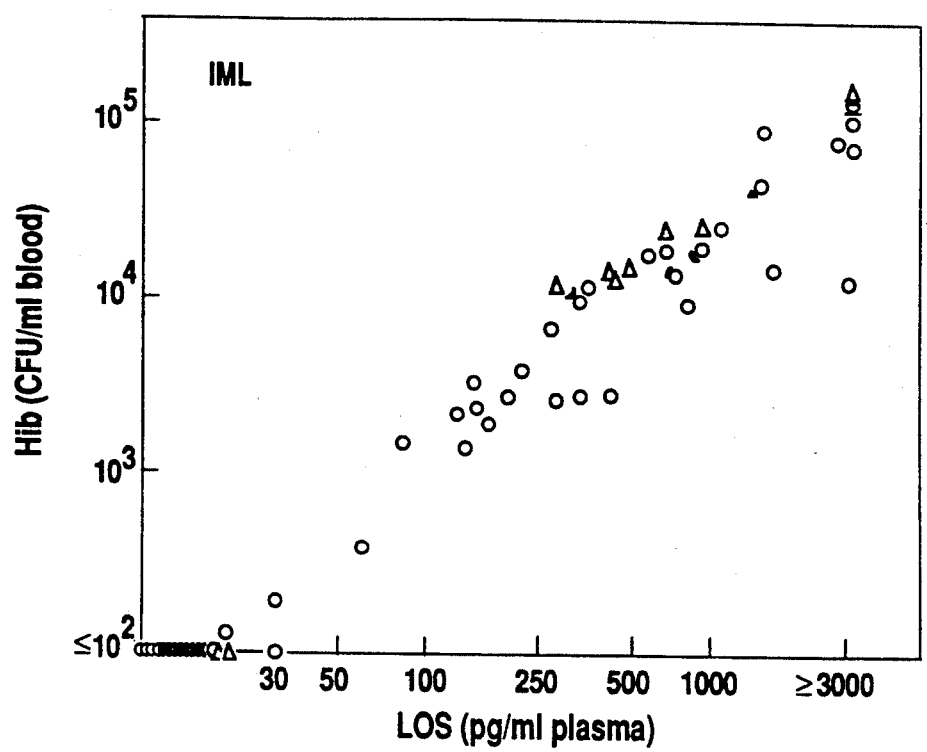
FIG. 3 shows levels of Hib DL42 (●) and DL301 (▲) bacteremia and concentrations of Hib LOS in infant rat plasma samples as detected by immunolimulus assay (r=0.845, p<0.001). Open symbols represent uninfected animals and are present only on the left side of the x-axis.

Forty-two (98%) of 43 rats with culture-proven Hib DL42 or DL301 bacteremia had detectable concentrations of LOS in their plasma by IML assay. Furthermore, there was a significant correlation (r=0.845, p<0.001) between the LOS concentrations measured and the magnitude of bacteremia in the animals. None of the uninfected rats had detectable LOS in their plasma samples, while one blood culture-negative sample from a rat challenged with Hib DL42 was positive with IML. There were no significant differences between the IML results obtained with the two different Hib strains DL42 and DL301, both of which are reactive with MAb 4C4 (FIG. 3).

Figure 4:
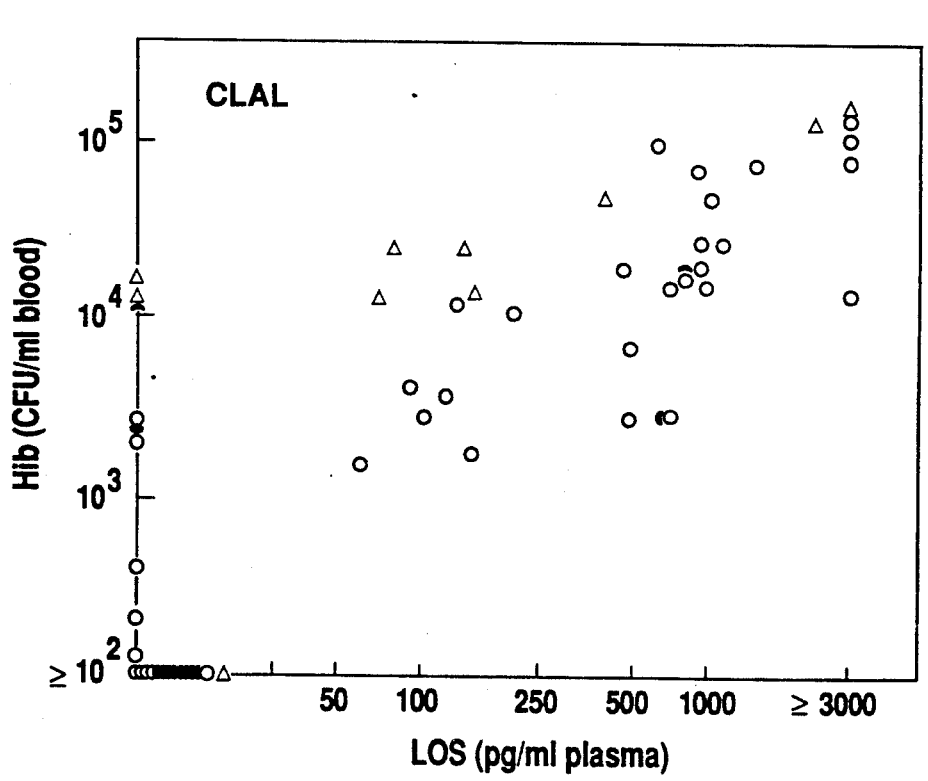
FIG. 4 shows levels of Hib DL42 (●) and DL301 (▲) bacteremia and concentration of Hib LOS in plasma samples as detected by CLAL assay (r=0.787, p<0.001). Open symbols represent uninfected infant rats and are present only on the left side of the x-axis.

The CLAL assay was positive with 27 (63%) of the Hib-infected rats, and negative with all those that did not have detectable bacteremia (FIG. 4). There was a significant correlation between the endotoxin concentrations measured with the CLAL assay and the levels of bacteremia (r=0.787, p<0.001); the correlation between IML and CLAL results was also significant (r=0.933, p<0.00).

EXAMPLE 4

Immunolimulus Assay for Hib LOS DL26 or *Escherichia coli* in Plasma From Rats Infected with These Bacteria All the rats infected with Hib DL26 (twelve animals) or *Escherichia coli* K1 (twelve animals) had detectable bacteremia and 19 (91%) of them had detectable concentrations of endotoxin when tested by CLAL (Table 2). However, all were negative with the IML assay using MAb 4C4; this particular MAb is not reactive with either of these strains (Table 2). Six of the nine *Escherichia coli* K1 infected rats, which had highest concentrations of bacteria in blood, had nonspecific positive result in the IML assay, reminiscent of the findings involving the effects of very high concentrations of LPS on the IML assay in earlier in vitro experiments (Table 1). When these plasma samples were retested in the IML at 1:10 and 1:100 dilutions, all of these samples yielded negative results in IML assay, thus confirming the specific nature of the assay. The results are presented in Table 2.

TABLE 2

Bacteremia, as detected by blood culture, and endotoxemia, as detected by chromogenic Limulus (CLAL) and by immunolimulus (IML) assays, in infant rats infected with Hib DL26 or *Escherichia coli* K1.

| | Hib DL26 | | | *Escherichia coli* K1 | | |
|---|---|---|---|---|---|---|
| Rat No. | Bacteremia (cfu/ml) | CLAL (ng/ml) | IML (ng/ml) | Bacteremia (cfu/ml) | CLAL (ng/ml) | IML (ng/ml) |
| 1. | $2.1 \times 10^5$ | 2.78 | <0.03 | $2.8 \times 10^7$ | >100 | <0.03 |
| 2. | $1.9 \times 10^5$ | 3.06 | <0.03 | $2.0 \times 10^7$ | >100 | <0.03 |
| 3. | $1.6 \times 10^5$ | 3.03 | <0.03 | $6.3 \times 10^6$ | >100 | <0.03 |
| 4. | $1.2 \times 10^5$ | 3.48 | <0.03 | $3.5 \times 10^6$ | 50.2 | <0.03 |
| 5. | $2.9 \times 10^4$ | 0.17 | <0.03 | $4.0 \times 10^5$ | 18.0 | <0.03 |
| 6. | $2.1 \times 10^4$ | 0.13 | <0.03 | $2.3 \times 10^5$ | 65.9 | <0.03 |
| 7. | $2.1 \times 10^4$ | 0.36 | <0.03 | $1.7 \times 10^5$ | 3.9 | <0.03 |
| 8. | $1.5 \times 10^4$ | 0.34 | <0.03 | $1.4 \times 10^5$ | 17.4 | <0.03 |
| 9. | $1.5 \times 10^4$ | 0.31 | <0.03 | $1.2 \times 10^5$ | 10.0 | <0.03 |
| 10. | $1.5 \times 10^4$ | 0.26 | <0.03 | ND[a] | ND | ND |
| 11. | $1.4 \times 10^4$ | <0.05 | <0.03 | ND | ND | ND |
| 12. | $9.2 \times 10^3$ | <0.05 | <0.03 | ND | ND | ND |

[a]Three rats died before sampling of blood.

PROPHETIC EXAMPLE 5

The present example outlines the procedure contemplated by the Applicants to be useful for the successful practice of detecting gram-negative bacterial lipopolysaccharides.

Detection of Gram-Negative Bacteremia, Septicemia, Endotoxemia and Detection of the Presence of Gram-Negative Bacterial Endotoxin in Fluids In this method, a monoclonal antibody or monoclonal antibodies broadly cross-reactive with essentially all LPS or LOS molecules of gram-negative bacteria will be employed as the capture agent. The general protocol to be followed is that described in the preceding examples. The antibody preferred for this particular method would be a mixture of antibodies including but not limited to, XMMEN-OE5, XMMEN-LY1, XMMEN-LY2, and XMMEN-J5D (11). These antibodies would be used to coat microtiter wells, the test fluid would then be subjected to heating at 75° C. for 12 min, and then reacted with the microtiter wells. After extensive washing of the wells, the Limulus lysate detection system would be added to the wells, followed by chromogenic substrate.

PROPHETIC EXAMPLE 6

The present example outlines the procedure contemplated by the Applicants to be useful in the detection of *Pseudomonas aeroginosa* and *Pseudomonas maltophila*.

Detection of *Pseudomonas aeruginosa* and *Pseudomonas maltophilia*

The monoclonal antibody XMMPS-605 (11) would be the appropriate capture agent for a system designed to detect the presence of the LPS of either *Pseudomonas aeruginosa* or *Pseudomonas maltophilia*. This antibody (XMMPS-6-5) could be used alone or in concert with the following monclonal antibodies: XMMPS-OP1, XMMPS-OP2, XMPPS-OP3, XMMPS-OP4 and XMMPS-OP7. These five additional monoclonal antibodies react with five of the seven Fisher types of *Pseudomonas aeruginosa* (11). In this particular method, the monoclonal antibody or antibodies would be used to coat microtiter plate wells. Then, as described for the examples cited above, these wells would be washed, the Limulus lysate detection system would be added, followed by the chromogenic substrate and color development measured and related to the amount of Pseudomonas LPS present.

The present invention has been described in terms of particular embodiments found or proposed by the present inventors to comprise preferred modes for the practice of the invention. It will be appreciated by those of skill in the art that, in light of the present disclosure, numerous changes and modifications can be made in the particular embodiments exemplified without departing from the intended scope of the invention. For example, other monoclonal or polyclonal antibodies could be used for the specific detection of Hib or other LOS. Fragments or functionally equivalent antibodies selective for endotoxin could be exchanged for the examples given. All such modifications are intended to be included within the scope of the appended claims.

REFERENCES

The literature citations appearing within the text of this application are hereby incorporated by reference to the extent they supplement, explain, provide a background for or teach methodology, techniques and/or compositions employed herein.

1. Bayston, K. F., Cohen, J. J. Med. Microbiol. 31, 73–83 (1990).
2. Morbidity Mortality Weekly Report 37/2, 31–34 (1990).
4. Jacobs, R. F., Sowell, M. K., Moss, M. M., Fiser, D. H. Pediatr. Infect Dis. J. 9, 196–200 (1990).
3. Ellner, J. J. Pediatr. Clin. North Am. 30, 365–371 (1983).
5. Cybulsky, M. I., Chan, M. K. W., and Movat, H. Z. Lab. Invest. 38/4, 365–378 (1988).
6. Levin, J. and Bang, F. B. Bull. Johns Hopkins Hosp. 115, 265–274 (1964).
7. deJongh-Leuvenink, J., Schellekens, J. and Verhoef, J. Infection and Immunity 58, 421–426 (1990).
8. Young et al., Clin. Res. 30/2, (April 1982).
9. Dunn, D. L., Bogard, W. C. and Cerra, F. B. Surgery 98, 283–90 (1985).
10. Salles, M.-F., Mandine, E., Zalisz, R., Guenounou, M. and Smets, P. J. Infect. Dis. 159, 641–647 (1989).

11. Young et al., U.S. Pat. No. 4,918,163, April 17, 1990.

12. Connelly, U.S. Pat. No. 4,906,567, Mar. 6, 1990.

13. Erich, T., Schellekens, J., Bouter, A., van Kranen, J., Brouwer, E., and Verhoef J. Immunol. 143, 4053-4060 (1989).

14. Pollack, M., Chia, J. K. S., Koles, N. L., Miller, M., and Guelde, G. J. Infect. Dis. 159, 168-188 (1989).

15. Teng, N. N. H., Kaplan, H. S., Hebert, J. M., Moore, C., Douglas, H., Wunderlich, A. and Braude, A. I. Proc. Natl. Acad. Sci. USA 82, 1790-1794 (1985).

16. Kirkland, T. N., Colwell, D. E., Michalek, S. M., McGhee, J. R. and Ziegler, E. J. J. Immunol. 137, 3614-3619 (1986).

17. Gulig, P. A., Patrick, C. C., Hermanstorfer, L., McCracken, G. H., and Hansen, E. J. Infect. Immun. 55, 513-520 (1987).

18. Hansen, E. J., Firsch, C. F., McDade, R. L., Jr., and Johnston, K. H. Infect. Immun. 32, 1084-1092 (1981).

19. Kimura, A., Patrick, C. C., Miller, E. E., Cope, L. D., McCracken, G. H., Jr., and Hansen, E. J. Infect. Immun. 55, 1979-1986 (1987).

20. Mertsola, J., Munford, R. S., Ramilo, O., Saez-Llorens, X., Nustafa, M. M., McCracken, G. H., Jr. and Hansen, E. J. J. Clin. Microbiol., submitted for publication.

Although the present invention has been described in some detail by way of illustration and examples to clarify and facilitate understanding, it will be obvious that certain changes and modifications may be practiced within the scope of the claims following.

What is claimed is:

1. A method of detecting bacterial endotoxin in a biological fluid, comprising the steps of:
    contacting a sample of biological fluid with at least one matrix-bound antibody which specifically binds an epitope of bacterial endotoxin to form a matrix-bound bacterial endotoxin;
    washing the matrix-bound bacterial endotoxin;
    incubating the matrix-bound bacterial endotoxin with an amoebocyte lysate to activate a protease system of the lysate;
    adding, to the lysate, a substrate of the protease system; and
    measuring amounts of a product formed from action of said protease system on the added substrate, said amounts being proportional to a level of bacterial endotoxin in the sample.

2. The method of claim 1 wherein the matrix-bound antibody specifically binds a core glycolipid of bacterial endotoxin.

3. The method of claim 1 wherein the matrix-bound antibody specifically binds an epitope comprising a region proximal to bacterial endotoxin lipid A.

4. The method of claim 1 wherein the matrix-bound antibody specifically binds an epitope comprising lipid A.

5. The method of claim 1 wherein the matrix-bound antibody specifically binds an epitope comprising a heptose and a keto-deoxyoctonate.

6. The method of claim 1 wherein the matrix-bound antibody comprises a binding fragment thereof.

7. The method of claim 1 wherein the bacterial endotoxin is a lipooligosaccharide or lipopolysaccharide of a gram-negative bacterium.

8. The method of claim 7 wherein the gram-negative bacterium is Escherichia, Bordetella, Branhamella, Salmonella, Haemophilus, Klebsiella, Proteus, Enterobacter, Pseudomonas, Pasteurella, Acinetobacter or Neisseria.

9. The method of claim 1 wherein the matrix-bound antibody is characterized as being directed toward an O-antigen.

10. The method of claim 9 wherein the matrix-bound antibody specifically binds Salmonella typhi O-antigen.

11. The method of claim 1 wherein the amoebocyte lysate is obtained from the blood of *Tachypleus tridentatus, Tachypleus gigas, Carcinoscorpius rotundicauda* or *Limulus polyphemus*.

12. The method of claim 1 wherein the substrate added to the reaction is a chromogenic substrate.

13. The method of claim 1 wherein the biological fluid is a sterile fluid or a fluid not normally containing a gram-negative lipopolysaccharide or oligopolysaccharide.

14. The method of claim 1 wherein the biological fluid is plasma, serum, cerebrospinal fluid or urine.

15. The method of claim 1 wherein the biological fluid sample is heated prior to contacting with the matrix-bound antibody.

16. The method of claim 15 wherein the heating is at a temperature of about 75° C.

17. A method of detecting *Haemophilus influenzae* type b oligosaccharide (Hib LOS) in biological fluids, comprising the steps of:
    contacting a sample of biological fluid with at least one matrix-bound antibody which specifically binds Hib LOS Lipid A-distal outer core oligosaccharide to form a matrix-bound Hib LOS;
    washing the matrix-bound Hib LOS;
    incubating the matrix-bound Hib LOS with Limulus amoebocyte lysate to activate a protease system in the Limulus amoebocyte lysate;
    adding to the lysate a substrate of the protease system; and
    measuring amounts of product formed from action of said activated protease system on the added substrate, said product being proportional to a level of Hib LOS in the sample.

18. The method of claim 17 wherein the matrix-bound antibody is an IgG3 monoclonal antibody which specifically binds an epitope in the oligosaccharide region of Hib LOS DL26 or Hib LOS DL42.

19. A kit useful for the determination of bacterial endotoxin in biological fluids which comprises:
    a carrier being compartmentalized to receive one or more container means in close confinement therein;
    a first container means comprising at least one antibody specifically binding to an epitope of an oligosaccharide proximal to lipid A or to lipid A within an inner core region of a gram-negative bacterium, said antibody being affixed to a solid matrix; and
    a second container means comprising an amoebocyte lysate; and
    a third container means comprising a chromogenic substrate for detecting release of a protease system by bacterial endotoxin.

20. The kit of claim 19 wherein the amoebocyte lysate is obtained from blood of *Tachypleus tridentatus, Tachypleus gigas, Carcinoscorpius rotundicauda* or *Limulus polyphemus*.

21. A kit useful for the determination of *Haemophilus influenzae* in biological fluids which comprises:
    a carrier being compartmentalized to receive one or more container means in close confinement therein;

a first container means comprising at least one antibody specifically binding to an epitope of the inner core oligosaccharide region distal to Lipid A of *Haemophilus influenzae* endotoxin, said antibody being affixed to a solid matrix;

a second container means comprising an amoebocyte lysate; and a third container means comprising a chromogenic substrate for detecting release of a protease system by bacterial endotoxin.

22. The kit of claim 24 wherein the antibody is an IgG3 monoclonal antibody which specifically binds an oligosaccharide epitope in Hib LOS DL42 or DL26.

23. The kit of claim 21 wherein the amoebocyte lysate, the chromogenic substrate and at least one antibody affixed to a solid matrix are supplied in lyophilized form.

* * * * *

UNITED STATES PATENT AND TRADEMARK OFFICE
CERTIFICATE OF CORRECTION

PATENT NO. : 5,198,339

DATED : March 30, 1993

INVENTOR(S) : Eric J. Hansen, et al

It is certified that error appears in the above-identified patent and that said Letters Patent is hereby corrected as shown below:

On the title page, under section [56] References Cited, insert all U.S. Patent Documents and Other Publications, which were previously submitted in an Information Disclosure Statement filed October 10, 1990 and in a Supplemental Information Disclosure Statement filed June 12, 1991 (copies of the 1449s initialed by Examiner are attached hereto) as follows:

U.S. PATENT DOCUMENTS

| | | |
|---|---|---|
| 4,918,163 | 04/17/90 | Young, et al. |
| 4,906,567 | 03/06/90 | Connelly et al. |
| 4,455,296 | 06/19/84 | Hansen et al. |

OTHER PUBLICATIONS

Bayston and Cohen, "Bacterial endotoxin and current concepts in the diagnosis and treatment of endotoxaemia", J. Med. Microbiol., Vol. 31, pp. 73-83 (1990)

Article in Morbidity Mortality Weekly Report, "Increase in National Hospital Discharge Survey Rates for Septicemia - United States, 1979-87" Vol. 39, No. 2, pp. 31-34 (January 19, 1990)

Jacobs et al., "Septic shock in children: bacterial etiologies and temporal relationships", Pediatr. Infect. Dis. J., Vol. 9, No. 3, pp. 196-200 (March 1990)

Ellner, J.J., "Septic Shock", Pediatric Clinics of North America, Vol. 30, No. 2 (April 1983)

UNITED STATES PATENT AND TRADEMARK OFFICE
CERTIFICATE OF CORRECTION

PATENT NO. : 5,198,339

DATED : March 30, 1993

INVENTOR(S) : Eric J. Hansen, et al

It is certified that error appears in the above-identified patent and that said Letters Patent is hereby corrected as shown below:

OTHER PUBLICATIONS (Continued)

Erich et al., "Binding Characteristics and Cross-Reactivity of Three Different Antilipid A Monoclonal Antibodies," J. Immunol., Vol. 143, No. 12, pp. 4053-4060 (Dec. 15, 1989)

Pollack et al., "Specificity and Cross-Reactivity of Monoclonal Reactive with the Core and Lipid A Regions of Bacterial Lipopolysaccharide," J. of Infect. Dis., Vol. 159, No. 2, pp. 168-188 (February 1989)

Teng et al., "Protection against gram-negative bacteremia and endotoxemia with human monoclonal IgM antibodies," Proc. Natl. Acad. Sci. U.S.A., Vol. 82, pp. 1790-1794 (March 1985)

Kirkland et al., "Analysis of the fine specificity and Cross-Reactivity of monoclonal anti-lipid A antibodies," J. Immunol., Vol. 137, No. 11, pp. 3614-3619 (December 1986)

Gulig et al., "Conservation of Epitopes in the Oligosaccharide Portion of the Lipooligosaccharide of *Haemophilus influenzae* Type b," Infect. and Immun., Vol. 55, No. 3, pp. 513-520 (March 1987)

Hansen et al., "Identification of Immunogenic Outer Membrane Proteins of *Haemophilus influenzae* Type b in the Infant Rat Model System," Infect. and Immun., Vol. 32, No. 3, pp. 1084-1092 (June 1981)

UNITED STATES PATENT AND TRADEMARK OFFICE
CERTIFICATE OF CORRECTION

PATENT NO. : 5,198,339                                               Page 3 of 6

DATED : March 30, 1993

INVENTOR(S) : Eric J. Hansen, et al

It is certified that error appears in the above-identified patent and that said Letters Patent is hereby corrected as shown below:

OTHER PUBLICATIONS (Continued)

Cybulsky et al., "Acute Inflammatin and Microthrombosis Induced by Endotoxin, Interleukin-1, and Tumor Necrosis Factor and their Implication in Gram-Negative Infection", Lab. Invest., V. 58, No. 4, pp 365-78 (1988)

Levin and Bank, "The Role of Endotoxin in the Extracellular Coagulation of Limulus Blood," F.B. Bull. Johns Hopkins Hosp., Vol. 115, pp. 265-274 (1964)

Jongh-Leuvenink et al., "Characterization of Anti-Core Glycolipid Monoclonal Antibodies with Chemically Defined Lipopolysaccharides," Infection and Immunity, Vol. 58, pp. 421-426 (February 1990)

Abstract by Young et al., "Monoclonal Antibody Directed Against the "Core" Glycolipid of Enterobacterial Endotoxin," Clinical Research Vol. 30, No. 2, 522A (April 1982)

Dunn et al., "Efficacy of type-specific and cross-reactive murine monoclonal antibodies directed against endotoxin during experimental sepsis," Surgery, Vol. 98, No. 2, pp. 283-90 (August 1985)

Salles et al., "Protective Effects of Murine Monoclonal Antibodies in Experimental Septicemia: *E. coli* Antibodies Protect Against Different Serotypes of *E. coli*," J. Infect. Dis., Vol 159, No 4, pp 641-47 (1989)

UNITED STATES PATENT AND TRADEMARK OFFICE
CERTIFICATE OF CORRECTION

PATENT NO. : 5,198,339

DATED : March 30, 1993

INVENTOR(S) : Eric J. Hansen, et al

It is certified that error appears in the above-identified patent and that said Letters Patent is hereby corrected as shown below:

OTHER PUBLICATIONS (Continued)

Kimura et al., "*Haemophilus influenzae* Type b Lipooligosaccharide: Stability of Expression and Association with Virulence," Infect. and Immunity, Vol. 55, No. 9, pp. 1979-1986 (Spetember 1987)

Mertsola et al., "Specific Detection of *Haemophilus influenzae* Type b Lipooligosaccharide by Immunoassay," J. Clin. Microbiol., submitted for publication Mutharia et al., "Monoclonal Antibodies Specific for *Escherichia coli* J5 Lipopolysaccharide: Cross-Reaction with Other Gram-Negative Bacterial Species," Infect. and Immun., Vol. 45, No. 3, pp. 631-636 (Sept. 1984)

Ziegler et al., "Treatment of Gram-Negative Bacteremia and Shock with Human Antiserum To a Mutant *Escherichia coli*," New England J. of Med., Vol. 307, No. 20 (November 1982)

Kirkland et al., "An Immunoprotective Monoclonal Antibody to Lipopoly-saccharide," J. of Immun., Vol. 132, No. 5, pp. 2590-2592 (May 1984)

Aydintug et al., "Cross-Reactivity of Monoclonal Antibodies to *Escherichia coli* J5 with Herterologous Gram-Negative Bacteria and Extracted Lipopolysaccharides," J. of Infect. Dis., Vol. 160, No. 5, pp. 846-57 (November 1989)

UNITED STATES PATENT AND TRADEMARK OFFICE
CERTIFICATE OF CORRECTION

PATENT NO. : 5,198,339

DATED : March 30, 1993

INVENTOR(S) : Eric J. Hansen, et al

It is certified that error appears in the above-identified patent and that said Letters Patent is hereby corrected as shown below:

OTHER PUBLICATIONS (Continued)

Bogard et al., "Isolation and Characterization of Murine Monoclonal Antibodies Specific for Gram-Negative Bacterial Lipopolysaccharide: Association of Cross-Genus Reactivity with Lipid A Specificity," Infect. and Immun., Vol. 55, No. 4, pp. 899-908 (April 1987)

Mertsola et al., "Specific detection of *Haemophilus influenzae* type b lipooligosaccharide by a polymyxin B monoclonal antibody assay," J. of Immunological Methods, Vol. 122, pp. 219-226 (1989)

Mertsola, J., Ramilo, O., Sáez-LLorens, X., Mustafa, G.H., McCracken, Jr., and Hansen, E.J., "Specific Detection of *Haemophilus influenzae* Type b Lipooligosaccharide (Hib-LOS) by Immunoassays", Interscience Conference for Antimicrobial Agents and Chemotherapy, August, 1989

Claim 8, line 68, column 13, and lines 1-3, column 14, italizes the words "*Escherichia, Bordetella, Branhamella, Salmonella, Haemophilus, Klebsiella, Proteus, Enterobacter, Pseudomonas, Pasteurella, Acinetobacter* or *Neisseria.*"

Claim 10, line 8, column 14, italize the words "*Salmonella typhi.*"

Claim 17, lines 34 and 36, column 14, italize the word "*Limulus.*"

UNITED STATES PATENT AND TRADEMARK OFFICE
CERTIFICATE OF CORRECTION

PATENT NO. : 5,198,339
DATED : March 30, 1993
INVENTOR(S) : Eric J. Hansen, et al It is certified that error appears in the above-identified patent and that said Letters Patent is hereby corrected as shown below:

Column 15, lines 1-11, delete the double spacing and replace with single spacing.

Claim 22, line 4, column 16, replace "24" with --21--.

Signed and Sealed this

Thirtieth Day of November, 1993

Attest:

BRUCE LEHMAN

Attesting Officer

Commissioner of Patents and Trademarks